United States Patent
Rafferty et al.

(10) Patent No.: US 6,416,709 B1
(45) Date of Patent: *Jul. 9, 2002

(54) PLURAL LAYERED METAL REPAIR TAPE

(75) Inventors: Kevin Rafferty, Harrison; Bruce Rowe, Cincinnati, both of OH (US)

(73) Assignee: C.A. Patents, L.L.C., Florence, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/504,126

(22) Filed: Feb. 15, 2000

Related U.S. Application Data

(63) Continuation-in-part of application No. 09/054,548, filed on Apr. 3, 1998, now Pat. No. 6,093,368, which is a continuation of application No. 08/863,612, filed on May 27, 1997, now Pat. No. 6,004,683, which is a continuation of application No. 08/444,156, filed on May 18, 1995, now abandoned, which is a continuation of application No. 08/147,716, filed on Nov. 4, 1993, now abandoned, which is a continuation-in-part of application No. 07/970,682, filed on Nov. 4, 1992, now abandoned.

(51) Int. Cl.[7] ............................... B22F 7/02; B22F 7/04
(52) U.S. Cl. ............................... 419/5; 419/8; 419/36
(58) Field of Search .................... 419/5, 8, 36

(56) References Cited

U.S. PATENT DOCUMENTS

| | | | | |
|---|---|---|---|---|
| 3,864,124 A | * | 2/1975 | Breton et al. ............... 75/212 |
| 4,031,279 A | * | 6/1977 | Cremer et al. ............... 428/44 |
| 4,194,040 A | * | 3/1980 | Breton et al. ............... 428/308 |
| 4,228,214 A | * | 10/1980 | Steigelman et al. ......... 428/212 |
| 5,264,011 A | * | 11/1993 | Brown et al. ............... 51/309 |
| 5,334,417 A | * | 8/1994 | Rafferty et al. ............. 427/253 |
| 5,348,215 A | * | 9/1994 | Rafferty et al. ............. 228/181 |
| 5,523,169 A | * | 6/1996 | Rafferty et al. ............. 428/551 |
| 5,577,655 A | * | 11/1996 | Mizuhara ..................... 228/56.3 |
| 5,867,762 A | * | 2/1999 | Rafferty et al. ............. 428/548 |
| 5,952,042 A | * | 9/1999 | Rafferty et al. ............. 427/189 |
| 5,997,604 A | * | 12/1999 | Rafferty et al. ............. 75/233 |

* cited by examiner

*Primary Examiner*—Daniel J. Jenkins
(74) *Attorney, Agent, or Firm*—Wood, Herron & Evans, LLP

(57) ABSTRACT

A base metal repair tape includes a first layer formed braze alloy bonded together with fibrillated polytetrafluoroethylene, a second layer formed from powdered base metal bonded together by fibrillated polytetrafluoroethylene and a third layer comprising a brazing alloy bonded together by fibrillated polytetrafluoroethylene. This is used to repair base metal by placing the first layer on the base metal and brazing the base metal powder so that the brazing alloy melts and diffuses into the base metal powder bonding it to the surface of the article. This permits the braze powder to be bonded to the base metal surface with minimal distance between the base powder particles. The number of alternating layers of base metal and braze alloy can be increased to increase the thickness of the repair. This can also be used to form small intricate parts.

5 Claims, 1 Drawing Sheet

PLURAL LAYERED METAL REPAIR TAPE

RELATED APPLICATION

This is a continuation-in-part of Ser. No. 09/054,548 filed Apr. 3, 1998 now U.S. Pat. No. 6,093,368 which is a continuation of Ser. No. 08/863,612 filed May 27, 1997 now U.S. Pat. No. 6,004,683 and a continuation of Ser. No. 08/444,156 filed May 18, 1995 now abandoned which is a continuation of Ser. No. 08/147,716 filed Nov. 4, 1993 now abandoned which is a continuation-in-part of application Ser. No. 07/970,682, filed Nov. 4, 1992, entitled "Metal Repair Tape," now abandoned.

BACKGROUND OF THE INVENTION

Metal parts, for example, those used in jet engines are generally required to meet very precise tolerances. Damage to metal parts during use or during machining where a part is overmachined can prevent the part from falling within the set tolerances and require that the part be repaired or replaced. To repair such damage, new metal must be brazed to the surface of the part.

The new metal needs to have a composition similar to the base metal. Thus, diffusion braze fillers are combined with powder base metal to provide a composition which brazes to the base metal at a temperature lower than the melting point or softening point of the base metal.

Typically, this was done by forming a slurry which includes the powdered base metal, powdered diffusion braze filler and a binder which could be, for example, a methacrylate binder, an alginate binder or the like. These systems provide acceptable results. However, well defined geometries needed for some repairs were very difficult to obtain.

Further, slurries such as these are difficult to use. The binder system must be initially mixed. Then the precise amount of base metal and diffusion filler must be combined. This has a very limited shelf life. It cannot be mass produced for sale and subsequent use. It must be prepared by the actual user which creates the potential problem of human error.

Also, the boron typically used in the braze alloy could localize or puddle on the surface of the part. This weakens the base metal and can destroy the part. Slurries are also difficult to conform, resulting in poor ability for large build-up repairs.

Also, with oxygen sensitive alloys such as those that include titanium, aluminum, hafnium, and chromium, heating above 800° F. can cause oxide formation. These oxides are not normally reducible in brazing furnaces. Most braze furnaces are designed to either operate in a vacuum or in a hydrogen atmosphere. However, there is frequently a trace amount of oxygen remaining in the furnace that can react with these metals. To avoid this problem, such alloys containing these oxygen sensitive metals are nickel coated prior to base metal repair. This nickel precoating is undesirable simply because it requires an extra step or even two extra steps frequently requiring masking of portions that are not to be nickel coated.

SUMMARY OF THE INVENTION

Accordingly, it is an object of the present invention to provide a base metal repair which is not a slurry and which does not require nickel precoating.

Further, it is an object of the present invention to provide such a base metal repair which provides precise dimensional repairs.

The present invention is a base metal repair tape which is a plural layered tape. At least one inner layer is formed from base metal powder bonded together by a binder such as fibrillated polytetrafluoroethylene. At least two layers are diffusion braze alloy also bonded together by a binder such as fibrillated polytetrafluoroethylene. The outer layers sandwich the inner layer. These layers are bonded together and can be placed directly on the repair area as a tape. During the thermal repair cycle, the diffusion braze alloy would melt and infiltrate the base metal tape from both sides providing a repair which would essentially keep its dimensional integrity as well as have a greater per volume density of basis metal.

Where geometries are complex, stresses placed on the tape during repair can cause the tape to lift away from the repair surface during the thermal processing. However using a three layered tape with a diffusion layer contacting the repair surface enhances wetability and reduces the possibility of tape movement. This lower layer is preferably maintained relatively thin to prevent damage to the repair surface. Since this lower layer is thin, there is little likelihood that boron will damage the base metal.

This tape provides a cleaning ability to repair surface as well as the base powder particles themselves. This can be extremely important where the base metal and the base metal powder of the repair contain high levels of aluminum and titanium which are potential oxide formers and potentially a threat to the success of the repair.

Further, the tape's cleaning ability reduces or eliminates the need for nickel plating over the part in the repair area due to the enhanced brazability.

Further, the resulting brazed metal structure is enhanced by the separation of the base metal powder and the diffusion metal powder. This is because using the current method, the distance between the base metal powder particles is reduced due to the separation of the components in the multi-layer tape. This creates a repair of more nearly part-like mechanical properties because of the higher base metal content per unit volume.

By holding at brazing temperature or slightly below for an extended period of time (e.g., 2 hours), the softening or melting point of the repair can approach the softening or melting point of the base metal, resulting in a higher quality repair, more closely approaching base metal properties.

The reason for the improvement stems from the outward diffusion of melting point suppressant away from the repair area, significantly reducing its concentration in the repair, and slightly raising it in the surrounding base metal.

Further, the flexible and pliable nature of the tape allows repairs of complex geometries to be easily addressed and promotes the easy manufacture of preforms for repairing multiple identical parts. Finally, after the polytetrafluoroethylene resin has been evacuated, the base metal tape geometry structure remains intact providing for near drawing dimensioned preforms reducing timely and costly machining of the repair area after repair thermal cycle.

In an alternate embodiment of the present invention, the tape can be formed with multiple alternating layers of base metal tape and diffusion braze alloy forming a tape which is greater than one-half inch thick. This can be cut to size to form intricate parts which can be machined to size and used.

These advantages of the present invention as well as others will be appreciated further in light of the following detailed description and drawings in which:

DETAILED DESCRIPTION

The present invention is a laminated tape 11 used for repair of hard metal surfaces 12, using a brazing technique. Hard metal surfaces or base metals include, of course, all forms of stainless steel, as well as nickel, cobalt, titanium, and tungsten based superalloys such as Rene 35, Rene 41, Rene 77, Rene 80, Rene 80H, Rene 95, Rene 125, Rene 142, Inconel 1606, Inconel 625, Inconel 713, Inconel 718, Hastelloy X, Wasp alloy, Haynes 188, L605, X-40, MarM-509, and MarM-247.

Figure 1:
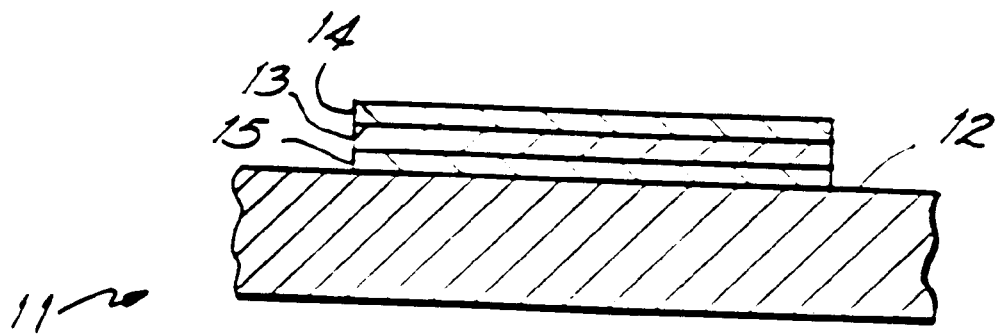
FIG. 1 is a cross-sectional view of the present invention.

As shown in FIG. 1, the laminate tape 11 is a three layered tape structure. The intermediate layer 13 is a mixture of the base metal powder and a binder. The outer two layers 14 and 15 are a mixture of diffusion braze alloy and binder.

There are a number of binders typically used to form braze tapes. Any of these binders typically used to form braze tape can be used. The preferred binder, however, is fibrillated PTFE. The fibrillated PTFE polymer used in the process of this invention is a high molecular weight PTFE resin produced by emulsion polymerization. These PTFE polymers have a broad molecular weight range of about 10–20 million and are commercially available products. Preparation of these polymers generally referred to as fluoropolymers, which is described in U.S. Pat. No. 2,510,112, U.S. Pat. No. 2,587,357, and U.S. Pat. No. 2,685,707, involves well known emulsion polymerization techniques wherein tetrafluoroethylene under pressure and water containing an emulsifying agent is reacted with a water soluble free radical catalyst. The emulsion produced is coagulated, washed and then dried. The average particle size of the polymer is about 50–560 microns. Polymer having larger or smaller average particle size is operative. The disclosure of these references are incorporated herein by reference.

The PTFE used to make the composition is commercially available from E.I. DuPont and Company, Wilmington, Delaware sold under the trade designation Teflon®6C. Each layer will have from 0.25 to about 25% of the fibrillated PTFE and preferably 1 to about 15% by weight. The preferred composition includes 3% PTFE by weight.

The second component of the intermediate layer 13 is the powdered base metal itself which will make up the remainder of the composition. Microstructural improvements can be observed in the base metal powder layer of the suggested multi-layer tape through the use of defined powder sizes.

Densification of base metal powder is achieved by having a particle size distribution such that the interstitial spaces between the larger particles are filled with smaller particles. Voided spaces to be filled by the diffusion alloy layer upon infiltration are minimized creating a repair area closer to base metal chemistry with a corresponding increase in desirable properties, for example, fatigue life. Also, while a theoretical distribution is desirable, a simple mixture of coarser powder, for example, −80 mesh to +180 mesh together with a finer powder, for example, −400 mesh, can significantly increase the base metal layers density without the greatly added cost of an engineering grade of powder.

The outer layers 14 and 15 again are formed from two components, the binder preferably fibrillated polytetrafluoroethylene and the diffusion braze alloy. A diffusion braze alloy is typically an alloy similar in composition to the base metal with the addition of a melt suppressant or it can be simply a braze alloy. There are many known commercially available braze alloys. The makeup of several of these compositions are listed below:

| | | |
|---|---|---|
| 1. | Boron | 2.9 |
| | Nickel | 92.6 |
| | Tin | 4.5 |
| 2. | Boron | 3.0 |
| | Chromium | 7.0 |
| | Iron | 3.0 |
| | Nickel | 83.0 |
| | Silicon | 4.0 |
| 3. | Chromium | 19.0 |
| | Nickel | 17.0 |
| | Silicon | 10.0 |
| 4. | Boron | 1.8 |
| | Nickel | 94.7 |
| | Silicon | 3.5 |
| 5. | Boron | 0.8 |
| | Cobalt | Balance |
| | Chromium | 19.0 |
| | Nickel | 17.0 |
| | Silicon | 8.0 |
| | Tungsten | 4.0 |
| 6. | Boron | 2.75 |
| | Chromium | 10.5 |
| | Nickel | 50.3 |
| | Palladium | 36.9 |
| | Silicon | 0.5 |

Such braze alloys can be purchased from companies such as Westgo, Praxair, and others.

To form the base metal intermediate layer 13 using the preferred binder, 1 to 6% of the fibrillated PTFE (Teflon®6C) is combined with 94 to 99% (by weight) of the ground metal in a ball mill or other low shear mixer such as a KD miller with kinetic dispersion or a vibratory mixer.

In a ball mill, the mixture is milled at about 200 rpm using ⅜ inch stainless steel balls. This is continued until the mixture changes from a powder to small agglomerated particles generally 10 to 40 minutes (25 minutes normally). If this is continued too long, a breakdown of the agglomeration occurs resulting in material unsuitable for tape product.

The mixture is then separated from the steel balls and rolled between adjustable rollers to a desired thickness. Specifically, the mixture is rolled between pressure rollers in a first direction, then the formed sheet is folded between pressure rollers in a first direction, then the formed sheet is folded and the folded sheet is roiled in a direction which is 90° from the axis of the first rolling step, i.e., cross rolled. Each rolling step decreases the thickness of the sheet. Preferably, the sheet is separated from the rollers by an aluminum foil separating sheet or other suitable material. This is continued until the desired thickness and consistency is obtained.

Likewise, the outer or diffusion braze alloy layers 14 and 15 are formed in the same manner as the base metal layer 13 by combining 1 to 6% polytetrafluoroethylene with 99 to 94% diffusion braze alloy (by weight). This is then mixed in a ball mill separated from the steel shot and rolled to the desired dimension.

In use, the ratio of braze alloy to base metal powder in the overall composite 11 should be from about 0.1 to 1.0 up to 0.1 to 0.1 with about 20% by weight of braze alloy and 80% base metal powder preferred. Increasing the ratio of braze alloy will decrease the braze temperature but the repair will be weaker. Also excess braze alloy will result in too much flow reducing the ability of the repair to maintain its shape.

Generally, the three layers 13, 14, and 15 are each formed to a thickness of about 0.001 to 0.06 inches or thicker and then are placed together with the diffusion braze alloy layers 14 and 15 sandwiching the base metal layer 15. These are passed together through rollers to reduce their overall thickness by about 50%. Thus, the final thickness of each layer will be about ½ the originally rolled thickness of the individual layers, i.e. 0.005 to 0.030" each. This can then be cut to the desired size for use. The thickness of the three layers along with the ratio of binder to base metal or diffusion braze alloys in the layers will control the ratio of diffusion braze alloy to base metal.

To use the composite 11, the damaged area of the base metal surface 12 is covered with the repair tape with diffusion layer 15 against the surface 12. The tape may be held to the base metal surface with an option adhesive layer (not shown) such as Nicrobraze 200 or using a two sided adhesive tape purchased from 3M. The thickness of the layers is established to provide the amount of base metal needed for the repair. The thickness of the base metal layer will generally be 0.005 to 0.030" although this may change depending on the application. The thickness of the diffusing braze alloy layers should be 0.0025 to 0.01 5".

The object is heated to a temperature of at least about 800° F. to 2300° F. which causes the binder to evaporate and the braze alloy to melt and infiltrate the base metal powder from above and below. For most nickel and cobalt alloys, at least 1750° F. is required. The braze alloy will then, upon cooling, bond the base metal powder to the metal surface.

By holding at brazing temperature or slightly below for an extended period of time, 30 minutes to 3 hours and preferably 2 hours, the softening or melting point of the repair can approach the softening or melting point of the base metal, resulting in a higher quality repair, more closely approaching base metal properties.

The reason for the improvement stems from the outward diffusion of melting point suppressant away from the repair area, significantly reducing its concentration in the repair, and slightly raising it in the surrounding base metal.

With alloys of titanium, aluminum, chromium, and hafnium, heating to a temperature above 800° F. causes oxide formation. With the present invention, the hydrogen fluoride generated as the tape is heated removes the oxides of these metals allowing a good braze joint without prior nickel plating. This will be further appreciated in light of the following example. Because microcrack cleaning is not required in this repair, the level of cleaning and reduced oxide formation from the structural tape itself is sufficient for an adequate repair.

Figure 2:
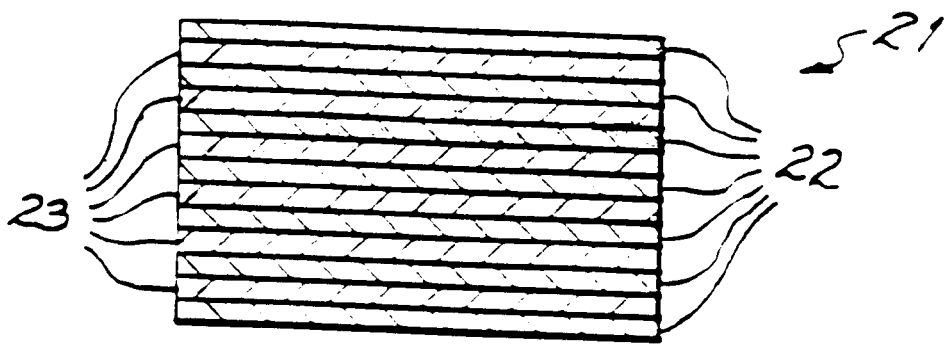
FIG. 2 is a cross-sectional view of an alternate embodiment of the present invention.

Multiple layer tape 21 can be prepared as shown in FIG. 2. In this FIG. 2, the tape 21 has thirteen layers, seven layers 22 of the diffusion braze alloy and six layers 23 of the base metal.

This composite tape again is made in the same manner as the tape shown in FIG. 1. The individual layers formed from the same proportions of base metal or diffusion braze alloy are combined with the fibrillated polytetrafluoroethylene and processed as previously described. The individual layers are combined together by running them through a press. With multiple layered tapes, the individual layers can be bonded together all at once or alternately can be combined two or four layers at a time from the middle portion towards the outer portion. This will compensate for the pressure differential which will be mainly felt on the exterior of the composite 21 as it passes through rollers.

The composite tape 21 shown in FIG. 2 in addition to providing a repair tape with extended thickness can also be used to actually manufacture parts or details of parts or assemblies. For example, sheet metal type parts can be readily produced using the multi-layered system by cutting a preform of the desired part from the tape 21 and processing the preform through an appropriate thermocycle producing a coherent article. This method could be extremely beneficial where a part has an intricate geometry, but can be easily cut from a sheet of tape as opposed to a complex and costly machining process.

As an example, the outer bands of jet engine nozzle assemblies which are about 0.25 inches thick can be formed by producing a composite tape preformed with Rene 80 powder and PTFE as the upper layer and a second layer of General Electric braze alloy, D 15, bonded together by PTFE. In this embodiment, the base metal layer could be, for example, 0.25 inches thick and the upper layer 0.063 inches thick. This would be formed into the shape of the finished band with some allowance for shrinkage, placed on ceramic blocks which have been machined to the outer band radius of the actual parts and subjected to a thermal cycle. If a thicker part were required, multiple layers of the base metal and diffusion alloy can be conbined to form the tape.

Accordingly, the present invention provides the ability to provide large base metal repairs on superalloys. It also is specifically beneficial for making base metal repair on superalloys where the surface being repaired has a complex geometry. In addition, this invention lends itself to the manufacture of intricate small parts and greatly simplifies this production method.

A further advantage of the present invention is that it at least partially separates the braze alloy from the surface of the article being repaired. Although a thin layer of the braze alloy may contact the surface, the majority of the braze alloy is separated from the part surface. The braze alloy itself can act to weaken the surface of the metal part. The preferred binder system for use in the present invention is fibrillated polytetrafluoroethylene. However, many of the advantages of the present invention will be appreciated employing any binder system typically used to form tapes for superalloy repair. However, by far the preferred embodiment of the present invention employs the fibrillated polytetrafluoroethylene as a binder. The invention itself, however, should be defined only by the appended claims wherein we claim:

What is claimed is:

1. A method of forming a superalloy base metal part for use on a jet engine comprising forming a flexible tape comprising braze alloy powder and oxygen sensitive superalloy base metal powder bonded together with 1% to 6% by weight of a fluoropolymer;

forming said tape to a desired size;

heating said tape to a temperature of 800° F. to about 2300° F.

2. The method claimed in claim 1 wherein said tape comprises a mixture of coarse powder base metal and finer powder base metal whereby interstitial basis of said coarse base metal powder are filled with said finer base metal.

3. The method claimed in claim 1 wherein said tape is first heated to a temperature of about 500° F. for one hour to provide stress release prior to subsequently heating said tape to a temperature of 800° F. to 2300° F.

4. The method of forming a superalloy base metal part for use in a jet engine comprising forming a flexible composite comprising braze alloy powder and oxygen sensitive superalloy base metal powder bonded together with 1%–6% by weight of a fluorocarbon polymer;

forming said composite to a desired size;

heating said composite to a temperature of about 800° F. to about 2300° F.

5. A method claimed in claim 4 wherein said fluoropolymer is a homopolymer of tetrafluoroethylene.

\* \* \* \* \*